(12) United States Patent
Pon et al.

(10) Patent No.: US 10,485,436 B2
(45) Date of Patent: Nov. 26, 2019

(54) SOUND-GENERATING DEVICE FOR IN UTERO INTERACTIONS WITH A DEVELOPING FETUS

(71) Applicant: UTI Limited Partnership, Calgary (CA)

(72) Inventors: Aura Pon, Calgary (CA); Johnty Wang, Calgary (CA)

(73) Assignee: UTI Limited Partnership, Calgary (CA)

( * ) Notice: Subject to any disclaimer, the term of this patent is extended or adjusted under 35 U.S.C. 154(b) by 107 days.

(21) Appl. No.: 15/577,878

(22) PCT Filed: May 27, 2016

(86) PCT No.: PCT/CA2016/050608
§ 371 (c)(1),
(2) Date: Nov. 29, 2017

(87) PCT Pub. No.: WO2016/191866
PCT Pub. Date: Dec. 8, 2016

(65) Prior Publication Data
US 2018/0146868 A1    May 31, 2018

Related U.S. Application Data

(60) Provisional application No. 62/168,440, filed on May 29, 2015.

(51) Int. Cl.
*A61B 5/024* (2006.01)
*A61B 5/00* (2006.01)
(Continued)

(52) U.S. Cl.
CPC ........ *A61B 5/02411* (2013.01); *A61B 5/4362* (2013.01); *A61B 8/0866* (2013.01);
(Continued)

(58) Field of Classification Search
CPC ..... A61B 5/02411; A61B 8/0866; A61B 5/11; A61B 5/4362; A61B 90/00; A61B 5/00;
(Continued)

(56) References Cited

U.S. PATENT DOCUMENTS 4,934,998 A * 6/1990 Thomas, Jr. ......... A61B 8/0866
600/27

FOREIGN PATENT DOCUMENTS

CN         104306018 A     1/2015

OTHER PUBLICATIONS

International Search Report and Written Opinion of the ISA/CA dated Aug. 9, 2016 in International Application No. PCT/CA2016/050608; 8pgs.

* cited by examiner

*Primary Examiner* — Mark Bockelman
(74) *Attorney, Agent, or Firm* — Haukaas Fortius PLLC; Michael H. Haukaas (57) ABSTRACT

This disclosure pertains to stimulation and monitoring devices for in utero cognitive stimulation of and interaction with developing fetuses by synthesizing sounds and sound patterns derived from movements of the fetuses' bodies and appendages. The exemplary stimulation and monitoring devices comprise arrays of sensors positionable above and/or the sides of the womb for detecting and recording movements of the fetus's body and appendages, one or more speakers, a microprocessor, controls, and optionally one or more light-emitting components. The collected movement data may be processed by a synthesizer for production of sound patterns and light patterns that are correlated with the movement data. The sound patterns and light patterns produced by the synthesizer may be transmitted through the speakers and the light-emitting components toward and into the womb to provide the development fetus with immediate (Continued)

cognitive stimulation in response to the movements of their body and appendages.

12 Claims, 8 Drawing Sheets

(51) Int. Cl.
    *G10H 1/00*         (2006.01)
    *A61B 8/08*         (2006.01)
    *G06F 3/16*         (2006.01)

(52) U.S. Cl.
    CPC .............. *G06F 3/16* (2013.01); *G10H 1/0066* (2013.01); *G10H 2220/371* (2013.01)

(58) Field of Classification Search
    CPC .......... G10H 1/26; G10H 1/0066; G10H 5/00; G10H 2220/371; G06F 3/16
    See application file for complete search history.

SOUND-GENERATING DEVICE FOR IN UTERO INTERACTIONS WITH A DEVELOPING FETUS

RELATED APPLICATIONS

This application is a National Stage filing under 35 U.S.C. § 371 of International Application No. PCT/CA2016/050608 filed May 27, 2016, which claims priority under 35 U.S.C. § 119(e) to U.S. Provisional Patent Application No. 62/168,440 filed May 29, 2015, which applications are incorporated herein by reference.

TECHNICAL FIELD

This disclosure relates to devices for interacting with in utero developing fetuses. More specifically, this disclosure pertains to sound-generating devices for in utero stimulation of, communication with, and interaction with developing fetuses.

BACKGROUND

It is well-known that fetuses have substantial capacities for movement, for learning, and for memory retention during in utero development prior to birthing. It is also known that the womb environment and external influences on the womb environment have powerful formative effects on fetal development and on fetal bonding with their mothers. A developing fetus can perceive and respond to sensory input from within and outside the womb primarily through tactile stimuli and auditory stimuli. Fetal hearing is considered likely to be the most developed of all the senses before birth. The gestation period from approximately 25 weeks through 6 months is the most critical to the development of the neurosensory components of the fetal auditory system, during which time stimulation in the form of speech, music, and meaningful environmental sounds is essential for the critical tuning of the hair cells in the cochlea to occur.

Outwardly perceivable deliberate fetal movements can be detected as early as 20 weeks, and this movement is a powerful mechanism for defining the fetus's body and sense of self as well as for engaging in "dialogue" with the outside world. Fetuses respond to stimuli such as their mothers' voices and sounds outside their wombs with deliberate movements and with physiological changes such as heart rate. Furthermore, it is apparent that in utero fetuses have postnatal memory retentions of repeated frequent stimuli such as lullabies sung repeatedly. Fetuses have even been conditioned to kick in response to controlled auditory and vibrotactile stimuli under experimental conditions.

Extrapolating from the numerous studies on fetal development could suggest that an unborn child not only has the basic potential for interaction with a specialized musical instrument, but also that its developing body and mind may thrive on such auditory and kinaesthetic interaction with the outside world.

SUMMARY

The embodiments of the present disclosure generally pertain to stimulation and monitoring devices for in utero cognitive stimulation of, communication with, and monitoring of, developing fetuses. According to some aspects, the exemplary stimulation and monitoring devices disclosed herein may generate and/or synthesize sounds in response to movements of fetus bodies and/or appendages. According to some aspects, the exemplary stimulation and monitoring devices disclosed herein may generate and/or synthesize lights of different colors in response to movements of fetus bodies and/or appendages.

Some embodiments of the present disclosure pertain to stimulation and monitoring devices that may be secured about a pregnant woman's abdomen by way of a wearable item of clothing or a wearable accessory. The exemplary devices may comprise one or more arrays of sensors positionable above and/or the sides of the womb for detecting and recording movements of the fetus's body and appendages, one or more speakers, and one or more arrays of light-emitting components. The movement data collected by the sensors may be processed by a synthesizer for production of sounds and sound patterns that are correlated with the movement data. The movement data collected by the sensors may be processed by a synthesizer for production of lights and light patterns that are correlated with the movement data. The sounds, sound patterns lights, and light patterns produced by the synthesizer may be transmitted through the speakers and the light-emitting arrays toward and into the womb to provide the development fetus with immediate cognitive stimulation in response to the movements of their body and appendages. According to some aspects, additional sounds, sound patterns, lights, and light patterns may be produced by the synthesizer in response to the fetal movements thereby allowing the fetus to generate movements to selectively produce or reproduce certain sounds and/or sound patterns and/or lights and/or light patterns. According to some aspects, the sounds, sound patterns, lights, and light patterns produced by the synthesizer in response to the fetal movements, may be communicated to one or more displays and sound systems for real-time observation by the pregnant woman and/or other observers. It is within the scope of the present disclosure for storage of the sounds, sound patterns, lights, and light patterns produced by the synthesizer in response to the fetal movements as digital data for subsequent access for playback and/or for assimilation into other output media.

Some embodiments of the present disclosure pertain to stimulation and monitoring devices for in utero cognitive stimulation of, communication with, and monitoring of developing fetuses by enabling the fetuses to control with their in utero movements, the types of sounds and/or lights generated and transmitted back into and toward the womb. The exemplary devices may be configured to receive recorded music and conversations for transmission through the speakers into the womb area for in utero cognitive stimulation of developing fetuses. In such applications, the sensor arrays will detect fetal movements in response to the recorded music and conversations, for signal processing, transmission, storage, and for synthesizing sound patterns and/or light patterns in response to the detected fetal movements.

BRIEF DESCRIPTION OF THE FIGURES

The present disclosure will be described in conjunction with reference to the following drawings in which.

DETAILED DESCRIPTION

The exemplary embodiments of the present disclosure generally pertain to stimulation and monitoring devices for in utero monitoring of, communication with, and cognitive stimulation of developing fetuses. The stimulation and monitoring devices may comprise sensors for detecting movements of the fetal body and its appendages. Some aspects generally pertain to stimulation and monitoring devices for in utero cognitive stimulation of, communication with, and monitoring of developing fetuses by enabling the fetuses to control with their in utero movements, the types sounds and or light patterns generated.

The exemplary stimulation and monitoring devices may comprise sound-generating components that are capable of projecting auditory signals from the external environment into a mother's womb in forms exemplified by recorded music, synchronous and asynchronous sound patterns, and conversational sound bites recorded by humans. The synchronous and asynchronous sound patterns may be generated by a synthesizer in response to and correlation with digital data generated from fetal movement analog signals detected by the sensors. The sounds and sound patterns may be basic sound units exemplified by individual discrete notes or pitches or chords or alternatively, a sequential series of complimentary notes or pitches or chords to generate recognizable repeating musical patterns or conversational patterns.

The exemplary stimulation and monitoring devices may comprise sound-generating components that are capable of generating synchronous and asynchronous sound patterns by a synthesizer in response and correlation to digital data generated from fetal movement analog signals detected by the sensors. The sounds and sound patterns may be basic sound units exemplified by individual discrete notes or pitches or chords or alternatively, a sequential series of complimentary notes or pitches or chords to generate recognizable repeating musical patterns or conversational patterns. The exemplary stimulation and monitoring devices may additionally comprise light-emitting components that project different colors of lights and light patterns from the external environment into the womb. According to some aspects, the sounds, sound patterns, lights, and light patterns produced by the synthesizer in response to the fetal movements, may be communicated to one or more displays and sound systems for real-time observation by the pregnant woman and/or other observers. It is within the scope of the present disclosure for storage of the sounds, sound patterns, lights, and light patterns produced by the synthesizer in response to the fetal movements as digital data for subsequent access for playback and/or for assimilation into other output media. The light patterns may be projected in cooperation with and coordination with projected auditory signals. Alternatively, the light patterns may be projected without concurrent projection of auditory signals.

An exemplary embodiment of the present disclosure pertains to a device for monitoring, stimulating, and communicating with in utero developing fetuses, wherein the device comprises a
  (1) belt component for fastening about a pregnant woman's abdomen,
  (2) one or more arrays of sensors positioned on the belt component for positioning above and/or about the womb when the belt component is worn by the pregnant woman,
  (3) a microprocessor for: (i) converting signals detected by the sensors in analog form into digital data, and (ii) transmitting the digital data to a receiver/transmitter by any of wired data transmission, optical fiber data transmission, and wireless data transmission,
  (4) one or more speaker components, and optionally
  (5) one or more light-emitting components.

The receiver/transmitter may be integrally incorporated into or onto the belt component and may communicate with the microprocessor by way of wired data transmission or by optical fiber data transmission. Alternatively, the receiver/transmitter may be a separate remote device that communicates with and cooperates with the microprocessor incorporated into/onto the belt component of the present device. The receiver/transmitter maps the digital data into parameters that trigger a synthesizer component to produce sound signals. The synthesizer can include either or both: (i) an embedded synthesizer system and (ii) an external sound-producing system exemplified by a Musical Instrument Digital Interface (MIDI) device such as an organ or a piano or a digital keyboard synthesizer, and alternatively, by (iii) a general purpose digital system capable of signal input, processing and synthesis exemplified by computers, tablets, smartphones and the like. Once synthesized, the sound signals are projected toward and into the womb from the speaker(s) incorporated into or onto the belt system. Alternatively, the sound signals produced by the synthesizer in response to the fetal movements, may be communicated to one or more displays and sound systems for real-time observation by the pregnant woman and/or other observers. The synthesized sound signals may be stored as sets in a database for subsequent playback on a speaker system. It is within the scope of the present disclosure to combine multiple sets of synthesized sound signals into an expanded playback set.

An embodiment of the present disclosure is use of the device disclosed herein for concurrently monitoring, communicating with, and stimulating a developing in utero fetus by concurrently detecting fetal whole body movements and movements of its appendages while projecting sound signals toward and into the womb, and alternatively, through one or more displays and/or speaker systems that are audible to the pregnant woman and other observers. The related digital data generated during a concurrent monitoring, communicating, stimulating event can be stored in a database, and may be subsequently analyzed for the purposes of detecting and correlating the fetus's motion responses with the sound signal patterns, and optionally, the light signal patterns during the event. A plurality of sets of digital data records generated during a plurality of monitoring, communicating, stimulating events can be stored in a database, and may be subsequently analyzed for the purposes of detecting and correlating the fetus's motion responses with the sound signal patterns and the light signal patterns during the events, to enable identification of fetal response patterns to certain types of sound signal patterns and to light signal patterns. Such correlations will enable the expectant mother to select specific sound signal patterns and optionally, if so desired, concurrent light signal patterns to provide calming and/or soothing signal projections to and about her womb. It is also within the scope of the present disclosure for a clinician to compare and correlate a plurality of in utero data sets generated for a first developing fetus with in utero data sets generated for one or more additional developing fetuses for the purposes of elucidating a developing fetus's in utero movements, and for diagnosing potential abnormalities.

One advantage of the device disclosed herein for concurrently, monitoring, communicating, stimulating a developing in utero fetus, is that the microprocessor may be programmed to generate sound signals and/or light signals in response to movements and/or gestures made by the fetal appendages thereby facilitating cognitive development. The fetal movements are carefully mapped to basic sound units, the building blocks of music, in a consistent and responsive way. The premise is that a developing fetus will comprehend after a number of repetitions, that a certain type of movement by one or more of its appendages will result in the generation of a specific type of sound signal or a sound signal pattern, and therefore, will be able to controllably repeat certain types of sound and light patterns.

A description of an exemplary stimulation and monitoring device for concurrently, monitoring, communicating, stimulating a developing in utero fetus, is now provided.

Figure 1:
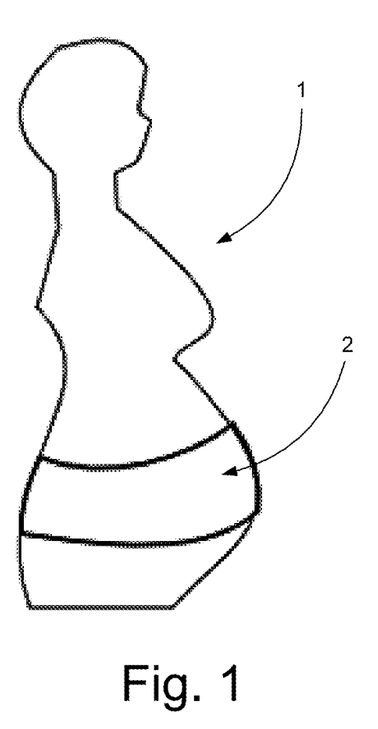
FIG. 1 is a side view of an exemplary stimulation and monitoring device disclosed herein, worn by a pregnant woman.
Figure 2:
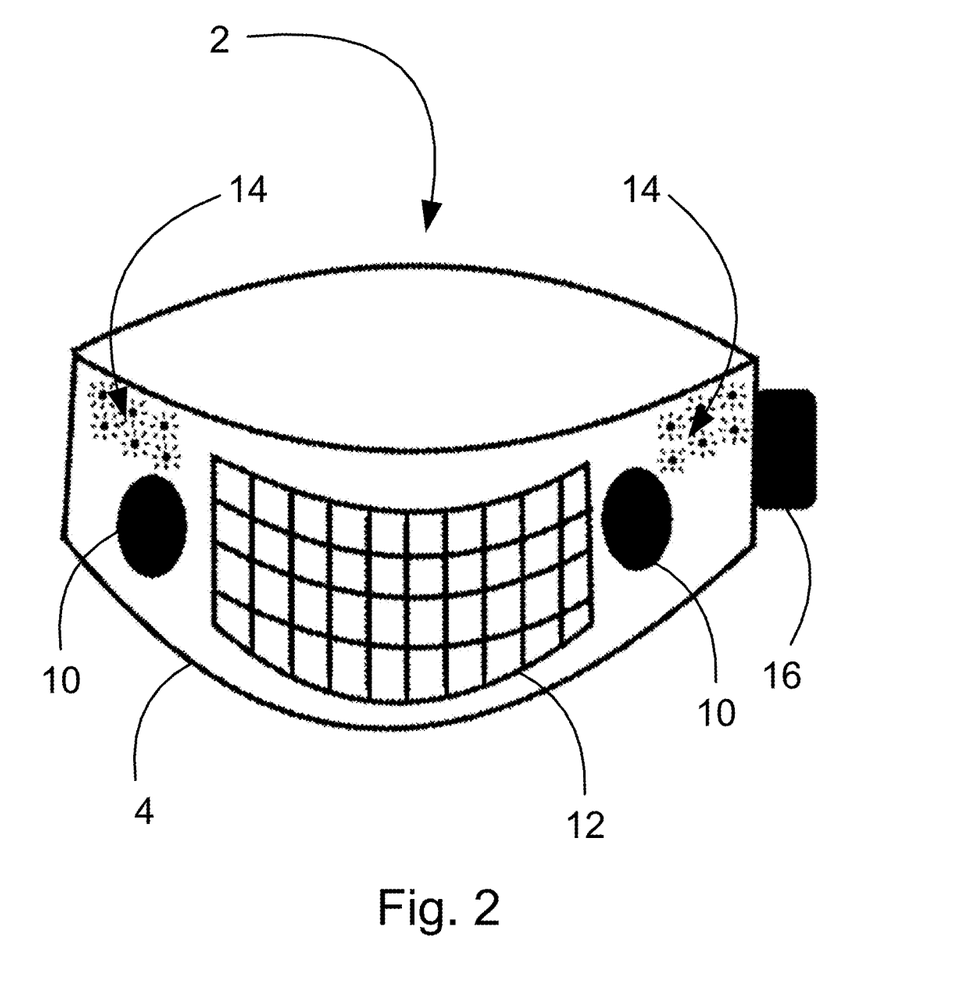
FIG. 2 is a perspective view of an embodiment exemplary stimulation and monitoring device illustrating suitable components incorporated thereinto.

One exemplary stimulation and monitoring device 2 according to the present disclosure is illustrated in FIGS. 1, 2, and 5-8 and generally comprises a size-adjustable flexible resilient abdominal belt 4 for securing around the abdomen of a pregnant woman 1 as illustrated in FIG. 1. The abdominal belt 4 may be constructed from a lightweight soft, breathable, pliable, light-permeable and washable material such as exemplified by nylon, polyamide, spandex, and the like. The abdominal belt 4 may be fabricated with a front side and a back side secured together by stitching. The front of the abdominal belt 4 is preferably of sufficient width to enable coverage of a pregnant woman's abdomen area through all stages of pregnancy. A pocket may be fabricated within the material at the front of the abdominal belt 4, to receive and house therein the electronic sensing and visualizing components (FIG. 2). It is to be noted that if so desired, the abdominal belt 4 component may be incorporated into articles of maternity clothing exemplified by panties, shorts, pants, and the like.

One or more sensor arrays 12 (FIG. 2) may be positioned about one area or optionally, two or more areas on the front and optionally sides of the abdominal belt 2, for the purpose of detecting movements of the fetal body and appendages. It is suitable to select sensors that are capable of sensing the magnitude and location of one or more fetal movements exemplified by "kicking" movements felt by a pregnant woman. Exemplary suitable sensor technology is exemplified by BEBOP SENSORS® (BEBOP SENSORS is a registered trademark of BeBop Sensors Inc., Berkeley, Calif., USA) and XSENSOR® LX100 sensors (XSENSOR is a registered trademark of Xsensor Technology Corp., Calgary, AB, Calif.). It is also suitable for a device of the present disclosure to have two or more types of sensor arrays, for example such as combinations of BEPOP SENSORS® and XSENSOR® LX100 sensors. It is to be noted that due to the varying types of movements that change according to different fetal movements as well as to changing conditions in the womb as the pregnancy progresses, multiple types of sensors may be combined into the abdominal belt so that a wide variety of movements can be detected with respect to location and pressures exerted. For example, sharp, jabbing movements are better sensed by fast response sensors such as those having piezoelectric transducers, while slower movements may be better detected by other types of sensors having force-sensitive resistors. Capacitive sensors may also be used.

One or more speakers 10 (FIG. 2) may be positioned adjacent to a sensor array 12, or optionally on either side of the sensor array 12, or optionally in between two spaced-apart sensor arrays (not shown). According to one exemplary embodiment, the speakers 10 may be in communication with a control box 16 (FIGS. 2, 5) either by wireless data transmission or alternatively, by wired data transmission within a wire plugged into the control box 16. The control box 16 may have a synthesizer (not shown) for generating, amplifying and projecting sound signals. A dedicated volume control 18 maintains safe volume levels for the fetus's developing auditory system independent of the output levels of the synthesizer.

At least one array of light-emitting components 14 is incorporated into a portion of the abdominal belt 2 approximate the front and/or sides (FIG. 2). The microprocessor can be provided with software that will cause the light-emitting component array 14 produce one or more colors of lights and/or light patterns in response to in utero fetal movements detected by the sensors 12.

Figure 3:
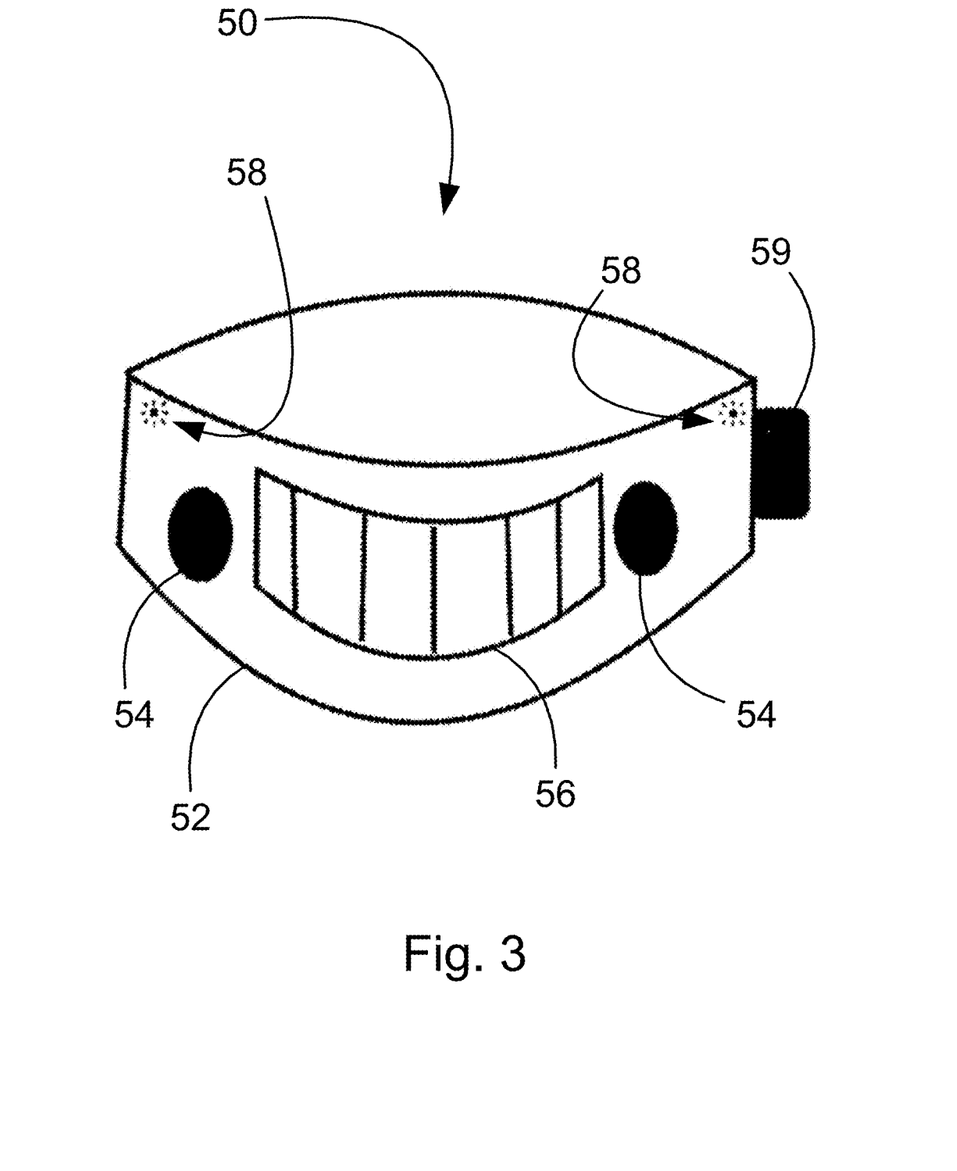
FIG. 3 is a perspective view of another embodiment exemplary stimulation and monitoring device illustrating suitable components incorporated thereinto.

Another exemplary stimulation and monitoring device 50 according to the present disclosure is shown in FIG. 3 and comprises a size-adjustable flexible resilient abdominal belt 52 for securing around the abdomen of a pregnant woman. A sensor array 56 is securely positioned on the abdominal belt 52 approximately mid-way between the ends of the belt, and a pair of speakers 54 are positioned on either side of the sensor array 56. A pair of light-emitting components 58 are positioned on the abdominal belt 52 with a speaker 54 interposed each light-emitting component 58 and the sensor array 56. A control box 59 is positioned on the abdominal belt 52 such that when the stimulation and monitoring device 50 is fastened onto a pregnant woman's abdomen, the control box 59 will be located about one of the woman's sides.

Figure 4:
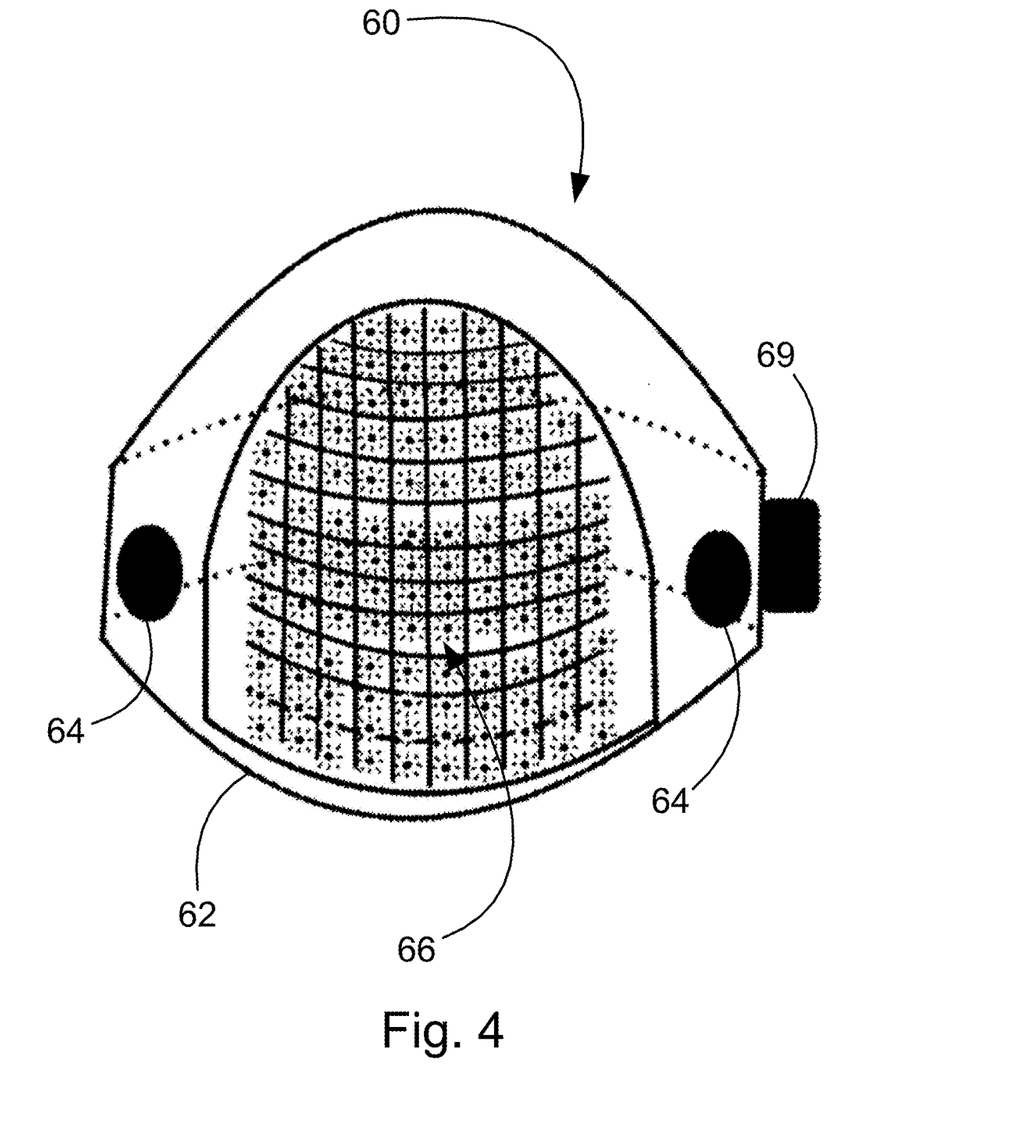
FIG. 4 is a perspective view of another embodiment exemplary stimulation and monitoring device illustrating suitable components incorporated thereinto.

Another exemplary stimulation and monitoring device 60 according to the present disclosure is shown in FIG. 4 and comprises a size-adjustable flexible resilient abdominal belt 62 for securing around the abdomen of a pregnant woman. This stimulation and monitoring device 60 has a much wider surface area for covering a larger portion of the pregnant woman's abdomen than would be covered by the exemplary stimulation and monitoring devices in FIGS. 2 and 3. A sensor array (not shown) is securely positioned on the abdominal belt 62 approximately mid-way between the ends of the belt. A large assembly i.e. array of light-emitting components 66 is overlaid onto the sensor array and extends around and beyond the sensor array so that generated patterns of colors and light can be projected into the womb from a larger surface area. A pair of speakers 64 may be positioned on either side of the sensor array 66. A control box 69 is positioned on the abdominal belt 62 such that when the stimulation and monitoring device 60 is fastened onto a pregnant woman's abdomen, the control box 69 will be located about one of the woman's sides.

Figure 5:
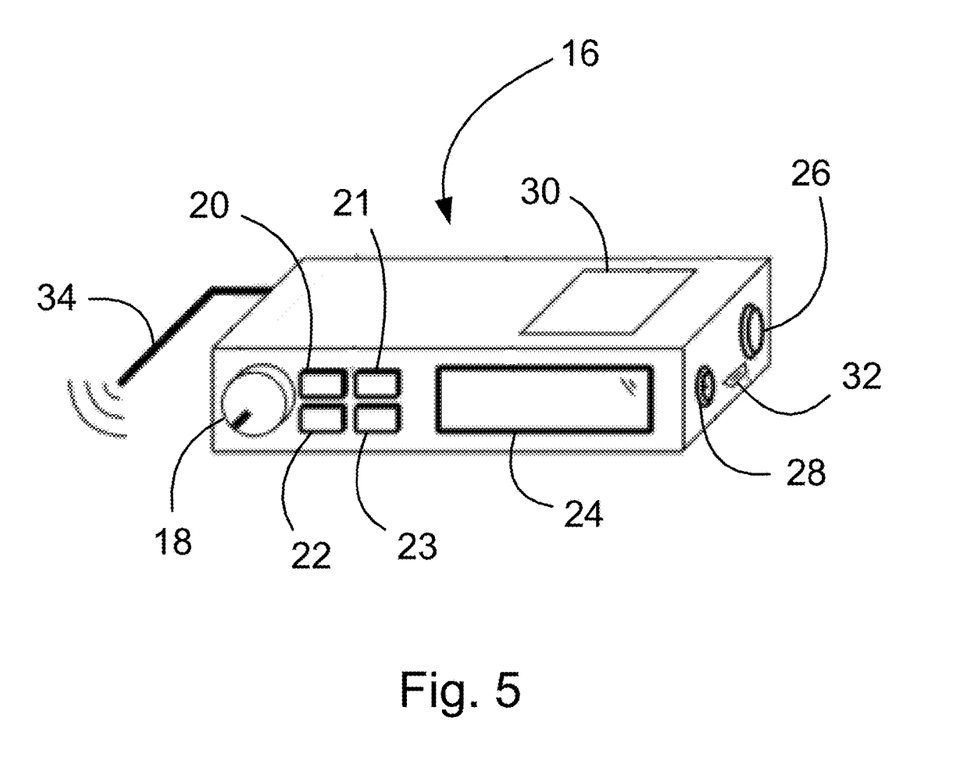
FIG. 5 is a perspective view of the control box component from the exemplary music device shown in FIG. 2.

The exemplary control boxes 16, 59, 69 (FIGS. 2, 3, 4 respectively) may be provided with an off/on switch 20, an operational mode "options" switch 21, a "confirm" switch 22 for confirming option selection, a recording switch 23, a volume control switch 18 for adjusting the output volume of the sound signals generated by the synthesizer (FIG. 5). In addition, a display 24 may be provided to show visual displays of motion detection, volume of sound patterns generated, intensity and colour of light signals generated, among others. As well, a battery pack 30 may be provided, along with a direct current power plug 28 for charging the battery pack 30. Also, an audio jack 26 may be provided for connecting the control box 16 to an external sound system or alternatively, a recording device. A USB port 32 may be provided for downloading recorded and or generated data to a memory stick or alternatively, for connection to an external synthesis module or processing module. An antenna 34 may be provided to facilitate wireless data transmission to an external microprocessor, alternatively to a synthesizer, alternatively to a mapping system.

Figure 6:
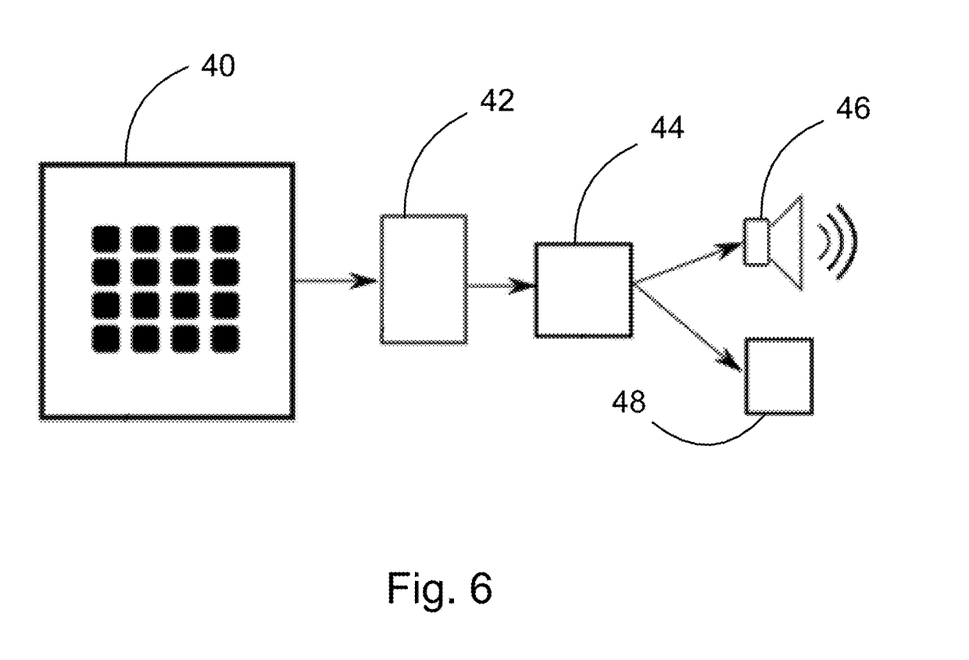
FIG. 6 is a schematic chart illustrating the communications between selected components of the exemplary music device shown in FIG. 2.

FIG. 6 is a schematic chart that illustrates the overall system disclosed herein. The sensor array(s) capture the locations and intensities of in utero fetal movements as analog signals that are processed to approximate levels by a signal conditioning circuit 42. The processed analog signals are converted into digital data by a microprocessor 44 housed within the control box. Additionally, the microprocessor 44 maps the detected fetal movements into synthesis control parameters, generates digitally synthesized audio output signals that correlate with the detected fetal movements. The digitally synthesized audio output signals are transmitted to the speaker system 46. The system also may include an output port(s) 48 for transfer of the detected data, processed data, and digitally synthesized audio output signals to, for example, a memory stick or to another microprocessor.

It is to be understood that the stimulation and monitoring devices and the systems disclosed herein facilitate at least two methods for digitally synthesizing audio output signals that are correlated to the detected motions of an in utero fetus. The first exemplary method comprises use of the synthesizer integrated into the belt component to generate a series of digitally synthesized sounds and/or sound patterns, then converting the digital data to analog signals that are then amplified for output by the speaker system integrated into the belt component. The second exemplary method comprises transmission of the processed analog signals relating to fetal movements, to an external device exemplified by synthesizers and MIDI-controlled stimulation and monitoring devices for generation of digitally synthesized audio output signals that are transmitted back to speaker systems integrated into the belt component.

Another exemplary embodiment relates to methods for mapping or translation between the input sensor signals and controls for sound output. First, the potential kinds of signals are classified and described followed immediately by possible mapping schemes for those signals that convert the sensor input into sound control parameters. These sound control parameters can then drive the internal synthesis system for audio output via the built in speakers, or an external device. At the most fundamental level, the sensor data coming from the belly can be considered as a 2D grid of continuous stream displacement values driven by movement of fetus that is sampled at a high interval (on the order of 100 Hz) with a response time on the order of a few milliseconds or less. The resolution of pressure signal depends on the physical specifications of the sensors and analog to digital circuitry, but for such applications anywhere between 8 to 10 bit signals are generally sufficient. The spatial resolution is usually a trade-off between number of detection positions, number of sensing elements, and overall required signal bandwidth. The kinds of signals can be considered as follows:

(i) discrete, simple threshold: translate sensor signal into discrete on/off events when a certain value is exceeded within a predefined grid area. This effectively creates a grid of "pads" on the mother's belly over the sensor's active area, and can generate instantaneous events or triggers. From these discrete events, stored audio samples can be triggered in the same way that an electric drum kit might emit sampled sounds when certain areas are activated. From these discrete events, it is also possible to control the state of the mapping (advancing through an auto-generated harmonic or melodic structure, pattern selection, or loop control);

(ii) discrete, threshold values with conditioning: due to potential sensor drift (changing of baseline values due to operating conditions or internal sensor characteristics), it may be necessary to process the sensor value using filtering techniques so that simple thresholded trigger events are created. The resultant events generated are the same as the previous section, but less prone to error;

(iii) discrete, threshold values with magnitude: from filtered or unfiltered thresholded values, the rate of change of displacement over a short window of time is used to calculate a velocity. In other words, in addition to the location of a trigger, its intensity is also calculated.

Simultaneously detected movements (e.g. fetal movement that creates detectable events on multiple locations) can trigger combinations of the above at the same time.

A more general view on the sensor data is a continuous X-Y position containing the pressure and location of the sensor grid. These continuous signals are discretized based on the resolution of the sensor grid. X-Y position of movement can control parameters such as: left-right panning of a sound, degree of effect (such as a modulation parameter in FM synthesis, level of reverberation, chorus or flanger effect). Position can also be used for frequency selection, either as a continuous range (sliding between notes), or quantized to nearest notes (glissando).

When integrated over time, a movement that causes the pressure on the belly to shift in space can be classified as a trajectory with intensity (pressure applied on sensor) and speed (the derivative of position over time). These can be mapped to higher order musical features such as the rate and direction of pitch trajectories The mappings described thus far are typically one-to-one, in the sense that a particular set of sensor input values correspond directly to a set of sound control parameters. More complex mapping scheme are possible if a higher level gesture recognition or classification algorithm is applied to the input signals. These are described under the topic typically named "Higher order mappings" or "Complex mappings" within the literature in the field of New Musical Instrument research.

Figure 7:
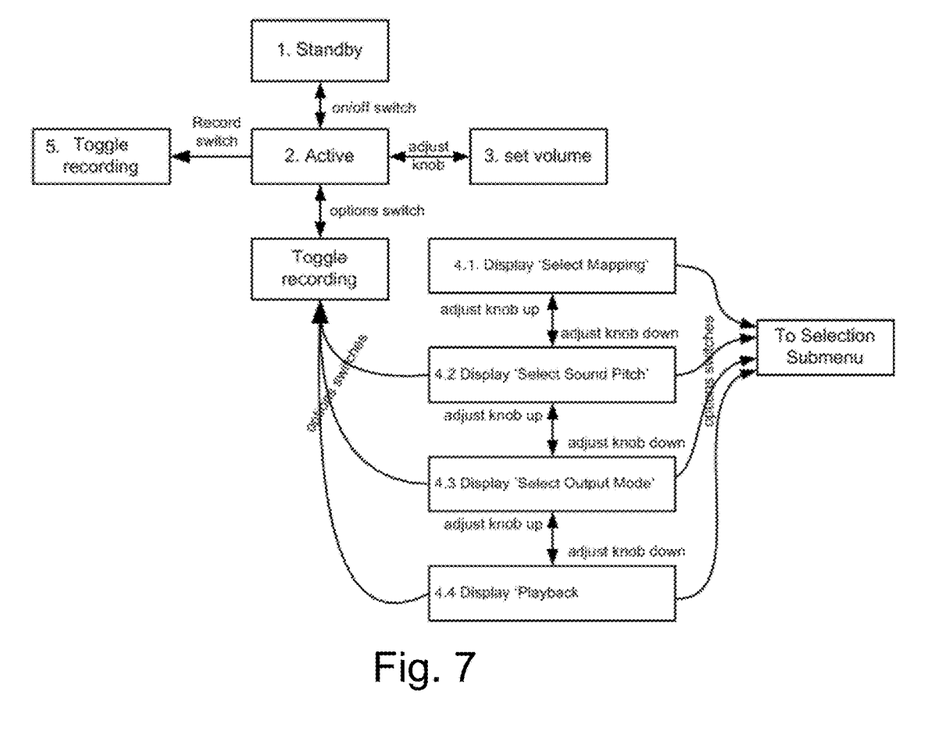
FIG. 7 is a schematic chart illustrating various internal operating modes of the exemplary music device shown in FIG. 2.
Figure 8:
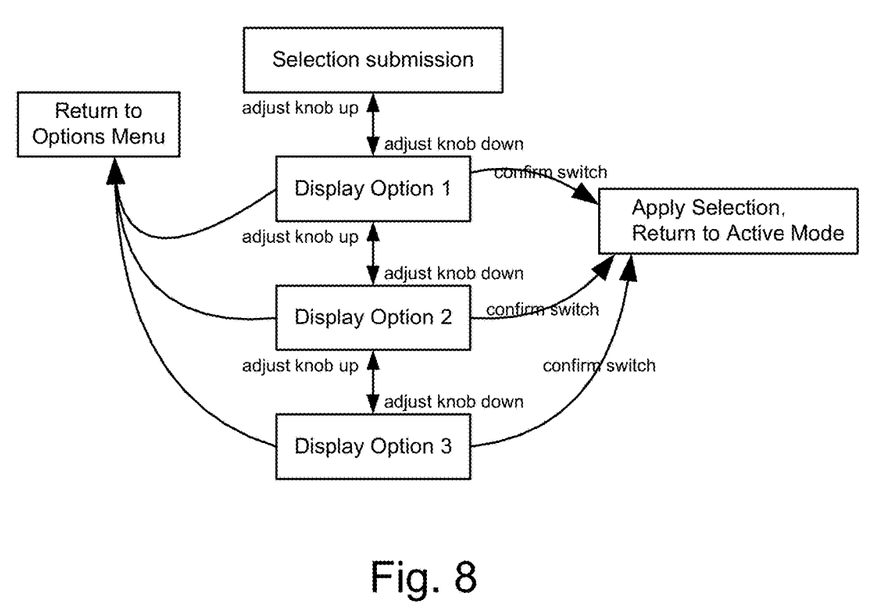
FIG. 8 is a schematic chart illustrating the structure of submenus for one of the internal operating modes.

FIG. 7 illustrates exemplary internal operating modes of the stimulation and monitoring devices disclosed herein that can be controlled via the user interface. When there is sufficient power provided either via the internal battery pack or external charger, the device is in "Standby" mode. The on/off switch could be wired in a way that either completely cuts off power to the device, or else toggle the system between the active operation mode and a low power state. When the on/off switch is depressed, the device transitions into the "Active" mode, where the device will load the previously used settings from memory and start receiving signals from the sensor and apply processing and mapping of the signals to output. The display screen will display the current status of the device with information such as selection of mapping and output sounds, volume level, battery level, and recording status. When the on/off is depressed again, the device goes back into "Standby" mode, and ceases operation. When the device is in "Active" mode, turning the rotary dial 10 (FIG. 5) will adjust the audio output level of the device. The set volume will be displayed on the display 24 (FIG. 5).

When the options button 21 (FIG. 5) is depressed during "Active" mode, the system transitions into "Options" mode, where the various device settings can be modified (FIG. 7; options box). From here, a second rotary dial (not shown in FIG. 5) can be used to navigate between each setting to be changed in reference to the options display 24, and the "confirm" button 22 selects the setting to be adjusted by opening a submenu (FIG. 7). Depressing the options button 21 will return the unit to the "Active" mode. Within each submenu (FIG. 8), a similar navigation procedure is used: the rotary dial can be used to navigate between each sub setting, pressing the "confirm" button selects the option, and pressing the "option" button returns the device to the previous level.

An exemplary device of the present disclosure can be used as follows. A pregnant woman may snugly attach the abdominal belt component around her waist, with the sensor array section arranged over her abdominal area. The user interface application is opened, and default settings are activated or the mother may adjust them. The woman switches on the power to the control box on the belt and adjusts the volume as desired. Movements made by the fetus will immediately trigger the embedded synthesizer to produce sounds out the embedded speaker system, and visualization of the movement will appear on the belt and the user interface application. For example, the baby's kick in the lower part of the woman's abdomen will trigger a simple musical sound such as one lower-frequency synthesized tone, with a loudness and panning corresponding the intensity and location of the kick, respectively. The woman may take further actions such as record the sensor data or audio of the child's movements.

Alternatively, after the abdominal belt is snugly attached around the pregnant woman's waist with the sensor array section arranged over her abdominal area, the user interface application is opened, and default settings are activated or the woman may adjust them. The woman switches on the power to the control box on the belt. Within the user interface application, the option is selected to use an external synthesizer, such as a MIDI-controlled pipe organ. Movements made by the fetus will immediately trigger the pipe organ to produce sounds, and visualization of the movement will appear on the belt and the user interface application. For example, the fetus rolls and the pressure from its back triggers a chord of pitches on the organ, with the stops selected, and thus the timbre of the sound, corresponding to the intensity of the movement.

Alternatively, after the abdominal belt is snugly attached around the pregnant woman's waist with the sensor array section arranged over her abdominal area, the user interface application is opened, and default settings are activated or the woman may adjust them. The woman switches on the power to the control box on the belt, and connects the control box to an external speaker system. The woman may select the timbre of sound for the fetus, such as a sample sound pattern, exemplified by a spectral pattern, from a saxophone. As used herein, "pattern" may mean a series of pitches and or rhythms. Depending on context, "pattern" as used herein refers to the spectral content of a particular timbre of sound. Movements made by the fetus will immediately trigger the embedded synthesizer to produce sounds out the external speaker system for an audience of people attending a concert, and visualization of the movement will appear on the belt and the user interface application, projected on a large screen on a stage. The mother and father may participate in music-making with the fetal child by touching the mother's belly and activating the sensor array, and additionally by playing other musical instruments, such as bass and drums, to add to the sounds made by the fetus. It is optional for the control box to have a microphone jack for engaging a microphone, or alternatively, be configured for wireless communication with a microphone to enable the mother and/or father to communicate with the fetus through the speaker component.

The invention claimed is:

1. A stimulation and monitoring device for interacting with an in utero developing fetus, the device comprising:
   a belt component for encircled engagement with a pregnant woman's abdomen;
   an array of sensor components incorporated into the belt component wherein the array is positionable above or adjacent to the pregnant woman's womb area when the belt component encircles her abdomen, said array configured to generate analog signals in response to movements by the fetus;
   at least one speaker component affixed to the belt component; and
   a control box associated with the belt component, the control boxing having
   (i) a receiver/transmitter for receiving the analog signals generated by the array of sensory components, the receiver/transmitter configured for additionally receiving analog signals and/or digital data from an external source,
   (ii) a microprocessor for converting the analog signals into digital data,
   (iii) a synthesizer for receiving said digital data and generating therefrom a series of digitally synthesized audio output signals, said synthesizer additionally configured to concurrently correlate and synchronize the digitally synthesized audio output signals with the analog signals received from the array of sensor components,
   (iv) a database component for receiving and storing therein the digitally synthesized audio output signals,
   (v) a power supply, and
   (vi) operating controls switches.

2. The stimulation and monitoring device of claim 1, wherein said at least one speaker component is positioned to direct sound signals toward the pregnant woman's womb area when the belt component encircles her abdomen.

3. The stimulation and monitoring device of claim 1, additionally comprising at least one light-emitting component affixed to the belt component and the microprocessor is in communication with the at least one light-emitting component.

4. The stimulation and monitoring device of claim 1, wherein the synthesizer is additionally configured to generate from said digital data, a series of digitally synthesized light output signals.

5. The stimulation and monitoring device of claim 4, additionally comprising at least one array of light-emitting components affixed to the belt component, said light-emitting components configured to receive the series of digitally synthesized light output signals and to produce therefrom a light display.

6. The stimulation and monitoring device of claim 5, wherein the light display is synchronized with the series of digitally synthesized audio output signals.

7. The stimulation and monitoring device of claim 1, wherein the control box is configured to receive and process digitally synthesized audio signals from an external source and to broadcast said processed audio signals through the at least one speaker component.

8. The stimulation and monitoring device of claim 7, wherein the digitally synthesized audio signals from an external source are selected from a group consisting of recorded music, recorded nature sounds, recorded patterns of soothing sounds, and voice recordings.

9. A series of digitally synthesized audio output signals generated by the stimulation and monitoring device of claim 1.

10. A compilation comprising two or more series of digitally synthesized audio output signals of claim 9.

11. The series of digitally synthesized audio output signals of claim 9, additionally comprising a series of digitally synthesized light output signals generated from the digital data.

12. A compilation comprising two or more series of digitally synthesized audio output signals and digitally synthesized light output signals according to claim 11.

* * * * *